United States Patent
Forslund et al.

(10) Patent No.: US 8,523,588 B2
(45) Date of Patent: Sep. 3, 2013

(54) IMPLANTABLE ELECTRIC LEAD

(75) Inventors: Mikael Forslund, Stockholm (SE); Per Jarl, Järfälla (SE); Marcus Helgesson, Danderyd (SE)

(73) Assignee: St. Jude Medical AB, Jarfalla (SE)

( * ) Notice: Subject to any disclaimer, the term of this patent is extended or adjusted under 35 U.S.C. 154(b) by 208 days.

(21) Appl. No.: 13/264,328

(22) PCT Filed: Apr. 29, 2009

(86) PCT No.: PCT/SE2009/000222
§ 371 (c)(1),
(2), (4) Date: Oct. 13, 2011

(87) PCT Pub. No.: WO2010/126403
PCT Pub. Date: Nov. 4, 2010

(65) Prior Publication Data
US 2012/0040547 A1 Feb. 16, 2012

(51) Int. Cl.
*H01R 13/28* (2006.01)
(52) U.S. Cl.
USPC ............. 439/289; 439/668; 439/909; 607/37; 607/122
(58) Field of Classification Search
USPC .......................................... 439/289, 668, 909
See application file for complete search history.

(56) References Cited

U.S. PATENT DOCUMENTS

| | | | |
|---|---|---|---|
| 4,572,605 A | 2/1986 | Hess | |
| 4,577,643 A | 3/1986 | Beranek | |
| 5,199,443 A | 4/1993 | Maurer et al. | |
| 5,252,090 A * | 10/1993 | Giurtino et al. | ............... 439/441 |
| 5,514,172 A | 5/1996 | Mueller | |
| 5,951,595 A * | 9/1999 | Moberg et al. | .................. 607/37 |
| 6,002,969 A | 12/1999 | Machek et al. | |
| 6,096,069 A | 8/2000 | Bischoff | |
| 6,501,990 B1 | 12/2002 | Sundberg et al. | |
| 6,951,266 B2 | 10/2005 | Tournier | |
| 7,158,837 B2 * | 1/2007 | Osypka et al. | ................. 607/122 |
| 7,794,256 B1 * | 9/2010 | Sochor | .......................... 439/289 |
| 2003/0036779 A1 | 2/2003 | Westlund et al. | |
| 2003/0077935 A1 | 4/2003 | Stein et al. | |
| 2005/0222634 A1 | 10/2005 | Flickinger et al. | |
| 2006/0030204 A1 * | 2/2006 | Jones et al. | ................... 439/488 |
| 2007/0276329 A1 | 11/2007 | Mernoe | |

OTHER PUBLICATIONS

Supplementary EP Search Report, dated Nov. 12, 2012—EP Application No. 09844108.2.

* cited by examiner

*Primary Examiner* — Truc Nguyen (57) ABSTRACT

An implantable lead has a distal lead portion with at least one electrode electrically connected to a connector ring through a conductor running in a lumen of the lead. A proximal lead portion includes the connector ring, a connector pin and a connector coupling mechanically and coaxially connected to each other with the connector coupling as a bridging element. A rotational lock in the form of a circumferential element of an elastically deformable, flexible material is provided in the connector coupling in the interface between the coupling and the connector ring. This rotational lock prevents any rotation of the connector pin to be propagated into a rotation of the connector coupling and consequently reduces the risk of damages to internal lead components due to any such unintentional coupling rotation.

10 Claims, 9 Drawing Sheets

Fig. 14

IMPLANTABLE ELECTRIC LEAD

BACKGROUND OF THE INVENTION

1. Field of the Invention

The present invention generally relates to implantable devices, and in particular to an implantable electric lead.

2. Description of the Prior Art

Various types of body-implantable electric leads are known and used in the medical field. For example, implantable medical devices, IMDs, such as pacemakers, cardiac defibrillators and cardioverters are, in operation, connected to implantable electric leads for sensing cardiac function and other diagnostic parameters and delivering stimulation pulses. For example, endocardial electric leads are attached at their proximal end to an IMD and at their distal end to the endocardium of a cardiac chamber.

In the art, multipolar leads comprise at least two electrodes in connection with their distal portion to be provided attached or close to the sensed and/or stimulated tissue. Consequently, these multipolar leads comprise at least two conductors running in the lumen of the lead body to electrically connect the electrodes with the IMD during operation. The conductors may be in the form of coils coaxially arranged in the lumen and electrically isolated from each other by an insulating sheath or tubing. This insulating tubing is attached, in the proximal portion of the lead, to a so-called connector coupling, which in turn is mechanically connected to a connector ring electrically connected to the outer conductor. When handling the implantable electric lead during implantation, the connector coupling and connector ring can be caused to rotate relative each other. Such unintentional rotation also rotates the insulating tubing, leading to a significant risk of breaks in the insulating tubing. The breaks in the insulating tubing will cause the implantable electric lead to short circuit between the two conductors, thereby preventing correct operation of the implantable electric lead and the IMD to which it should be connected.

SUMMARY OF THE INVENTION

It is an objective to provide an implantable electric lead with reduced risk for damages to internal lead parts due to unintentional rotation of lead components.

Briefly, the above object is achieved in accordance with the invention by an implantable electric lead adapted for connection to an implantable medical device that has a lead body with a distal lead portion and a proximal lead portion. The distal lead portion has at least one electrode electrically connected to lead components in the proximal lead portion through at least one conductor running in the lumen of the lead body.

The proximal lead portion has a connector pin connectable to the implantable medical device and preferably electrically connected to an inner conductor running in the lead body lumen. A connector ring is provided in the proximal lead portion and is electrically connected to an electrode in the distal lead portion through the conductor, which is preferably coaxially arranged in the lumen relative the pin-connecting conductor. The connector pin and connector ring are mechanically interconnected through an insulating connector coupling provided in order to restrain any axial movement of the proximal lead portion components.

A rotational lock in the form of a circumferential or circumferentially distributed element of an elastically deformable, flexible material is arranged in the connector coupling in the interface between the coupling and the connector ring. The rotational lock restrains any rotation of the connector coupling relative the connector ring.

This rotation restriction is important in connection with implantation of the lead. Otherwise a rotation of the connector pin may propagate into a rotation of the connector coupling and its attached lead components, which thereby can break due to the unintentionally applied torque. The rotational lock effectively prevents the rotation of the connector pin to propagate into an unintentional rotation of the connector coupling and consequently reduces the risk of damages to internal lead components during implantation.

The rotational lock preferably operates as friction lock and is being compressed tightly between the connector ring and coupling. In a preferred but optional embodiment, the rotational lock is in the form of a sealing ring of the elastically deformable, flexible material coaxially positioned around the connector coupling. The rotational lock will then have dual functions, both rotation restriction and sealing of the interior of the lead from the outside.

An embodiment also relates to a method for assembling the implantable electric lead.

DESCRIPTION OF THE PREFERRED EMBODIMENTS

Throughout the drawings, the same reference numbers are used for similar or corresponding elements.

The present invention generally relates to an implantable electric lead or catheter, and in particular such implantable electric lead adapted for connection to an implantable medical device (IMD), such as a pacemaker, cardioverter or defibrillator, for the purpose of applying stimulating pulses to a target tissue in a subject and/or sensing electric signals from the tissue.

In more detail, the invention relates to a technique that can be applied in the implantable electric lead in order to prevent or at least reduce the risk of breaks in internal lead parts in connection with implantation of the implantable electric lead. This technique is based on providing a rotational stop or lock in the interface between specific lead elements present in the IMD connecting part of the lead. This rotational lock restrains and restricts any rotation between the lead elements that otherwise can occur in the prior art leads.

The present invention will be mainly be described in connection with an implantable electric lead adapted for implantation inside or in connection with an animals heart, preferably a mammalians heart and more preferably the heart of a human patient. The lead can therefore advantageously be a so-called intracardiac lead, an endocardial lead or an epicardial lead. The embodiments of the invention are though not limited to such cardiac leads but can instead be used in connection with any implantable electric lead or catheter regardless of the intended implantation site. Thus, the lead could therefore be implanted in connection with a subject's brain, nervous tissue, spinal cord, muscles, etc.

Figure 1:
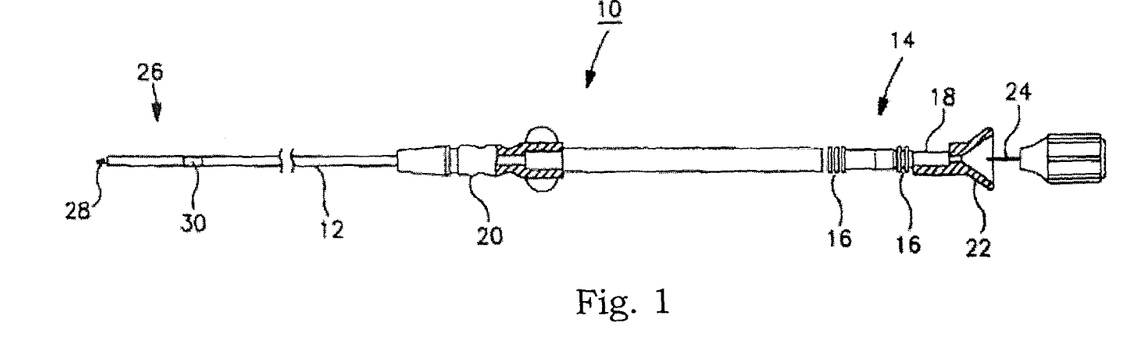
FIG. 1 is an illustration of an implantable electric lead according to an embodiment.

FIG. 1 schematically illustrates an implantable electric lead 10 according to an embodiment. The lead 10 has a flexible, elongated lead body 12 covered by an insulative sleeve or tubing made of, for example, polyurethane, silicone rubber or a mixture thereof. A terminal assembly or proximal lead portion 14 is provided at the proximal end for coupling the lead 10 to an IMD (not shown.) The proximal lead portion 14 has sealing rings 16 of a type known in the art and terminal or connector pin 18.

An optional anchoring sleeve 20, shown partially in cross-section, may be provided for suturing the lead body 12 to body tissue following implantation. The anchoring sleeve 20 is preferably fabricated from silicone rubber, although it may also be constructed of any other suitable biocompatible material known in the art.

The lead 10 may also be connected to a stylet guide 22 through the connector pin 18. This stylet guide 22 is used together with a stylet assembly 24 for imparting stiffness to the lead 10 during placement. The stylet guide 22 and the stylet assembly 24 are typically discarded after use and before connection of the connector pin 18 to the IMD.

An electrode and fixation assembly or distal lead portion 26 is provided at the distal end of the lead body 12. The distal lead portion 26 is, in the disclosed embodiment, of the bipolar and active type and has a helix 28 at its distal end and a ring electrode 30 spaced proximally back from the distal end. The helix 28 typically constitutes one of the electrodes, optional in electrical connection with a tip electrode, of the lead 10, with the ring electrode 30 being a second electrode. As will be appreciated by those of ordinary skill in the art, the helix 28 and the ring electrode 30 are coupled to separate, insulated conductors which extend along the length of the lead body 12. Conductors are preferably configured as concentric multifilar coils of MP35N, 35N LT or any other suitable alloy, such as a platinum-iridium alloy. This configuration allows for a longitudinal lumen to exist along the length of the lead body 12, such that the stylet assembly 24 may be received therein.

The implantable electric lead 10 illustrated in FIG. 1 should merely be seen as an illustrative example of a lead according to the invention. For instance, leads 10 having more than two electrodes 28, 30 at the distal lead portion 26 can be used. Thus, the lead 10 is preferably a so-called multipolar lead.

Figure 2:
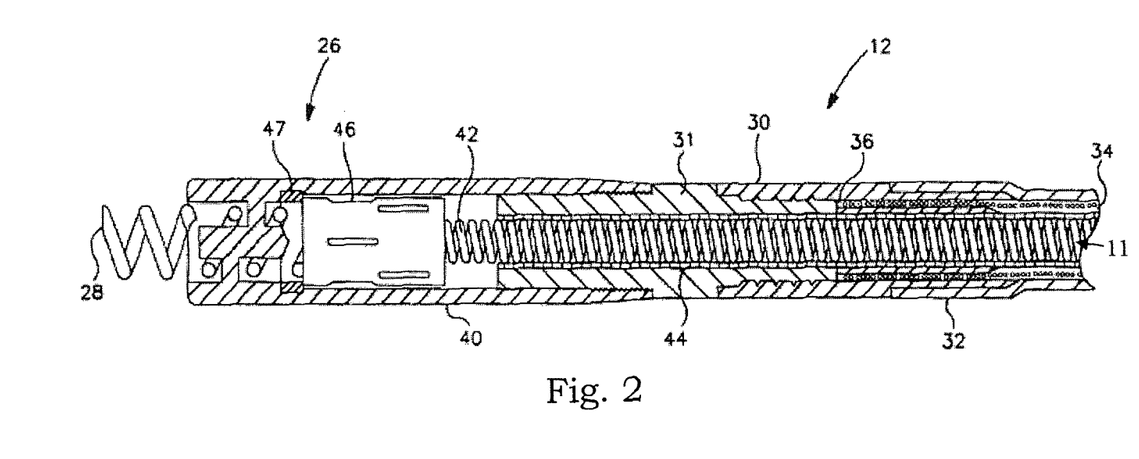
FIG. 2 is a cross-sectional view of a distal portion of an implantable electric lead according to an embodiment.

FIG. 2 illustrates a greatly enlarged cross-sectional side view of the distal lead portion 26 and lead body 12 in FIG. 1. As seen, the lead body 12 has an outer flexible insulative sheath 32 made of, for instance silicone rubber, polyurethane, a mixture thereof, or the like. The outer insulative sheath 32 covers a first, outer coiled conductor 34. The outer conductor 34 extends along through the lead body 12 in its lumen 11 and terminates at its distal end where it is electrically coupled, for example by spot or laser welding, to a crimp sleeve 36. The crimp sleeve 36, in turn, is in electrical connection with a ring electrode 30.

Partially engaged between the ring electrode 30 and the helix 28 is a ring/spacer assembly 31 that is coupled to a tip/ring spacer 40, which is typically made of silicone rubber. In addition to establishing a predetermined distance between the ring electrode 30 and the helix 28, the tip/ring spacer 40 functions to define a substantially cylindrical chamber in which the remaining components are disposed as well as to define the outer surface of the distal lead portion 26. In the disclosed embodiment, the tip/ring spacer 40 has dimensions such that a constant lead body diameter is maintained between the helix 28 and the ring electrode 30.

Extending along the length of the lead body 12 through the crimp 36, the ring electrode 30, the ring/spacer assembly 31 and the tip/ring spacer 40 is a second, inner coiled conductor 42, which is insulated from the outer coiled conductor 34 by an inner insulative sheath or tubing 44 which, like the outer sheath 32 can be made of silicone rubber, polyurethane, a mixture thereof, or the like. The inner conductor 42 terminates at a substantially cylindrical crimp bus 46. The crimp bus 46, in turn is coupled to the helix 28. Located distal to the crimp bus 46 is an optional indicator ring 47 to provide a radiopaque indication of how far extended the helix 28 is from the lead body 12. The helix 28 has the dual function of fixing the lead to the myocardium and functions as a pacing/shocking electrode.

The implantable electrode of the invention can also be used in other active fixation leads than the one illustrated in FIG. 2, i.e. having another set of distal lead components.

Figure 3:
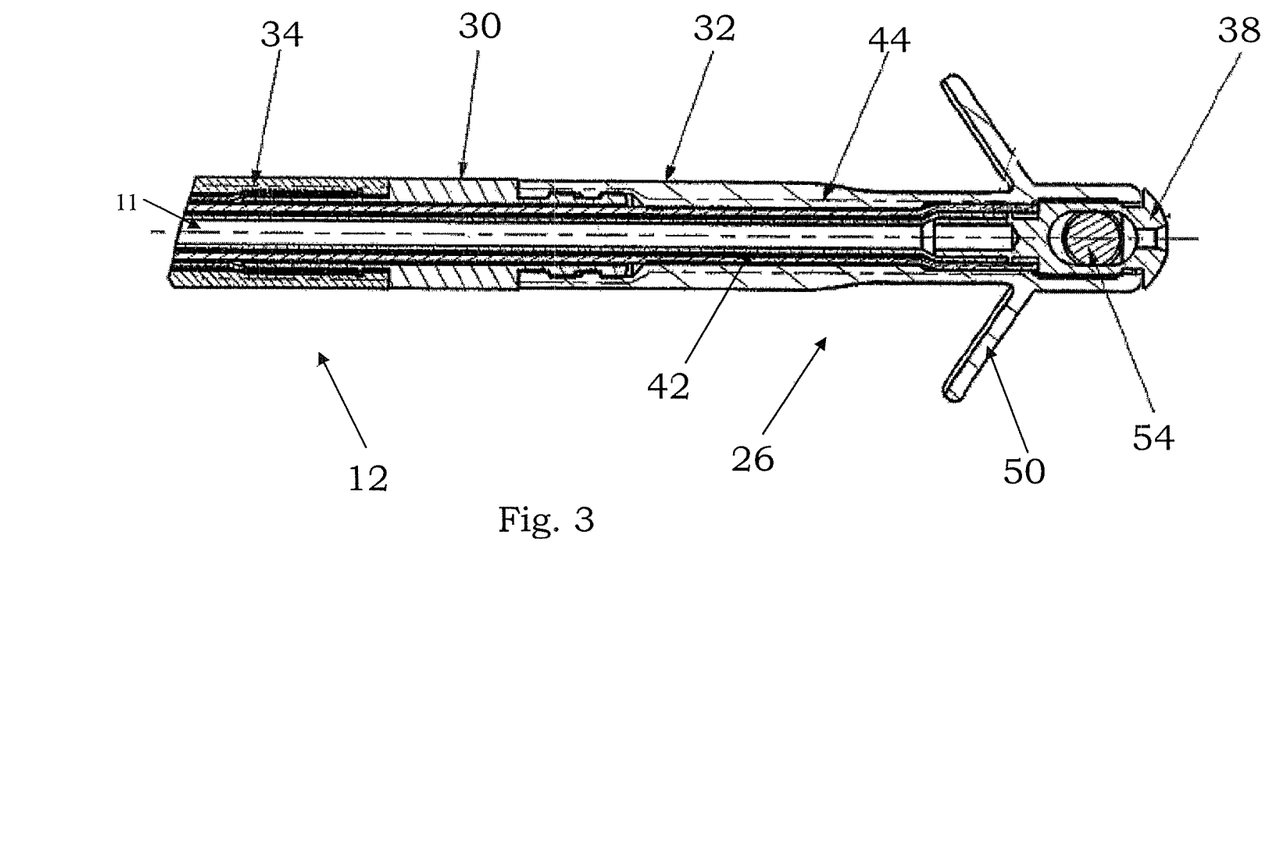
FIG. 3 is a cross-sectional view of a distal portion of an implantable electric lead according to another embodiment.

FIG. 3 illustrates an enlarged cross-sectional view of an implantable electrical lead of passive fixation type. The lead body 12 has an outer flexible insulative sheath 32 covering a first, outer coiled conductor 34 extending along the lead body 12 in the lumen 11 and terminating at a ring electrode 30 or electrically coupled to the ring electrode through a crimp sleeve (not illustrated).

A second, inner coiled conductor 42 is electrically insulated from the outer conductor 34 by an inner insulative sheath 44. The inner conductor 42 is electrically connected to a tip electrode 38. The lead tip may also optionally be equipped with a steroid plug 54, the use of which is well known in the art. Passive fixation of the lead at a correct position in a patient body is achievable by a tine assembly 50.

The embodiments can also be used in other passive fixation leads than the one illustrated in FIG. 3, i.e. having another set of distal lead components.

The implantable electric lead of the invention described and disclosed above can, in operation, be connected to an IMD. The IMD could be a pacemaker, cardiac defibrillator or cardioverter. In such a case the IMD has at least one connected lead with electrodes and/or sensors for performing the therapy and/or monitor function to the heart. However, the present invention is not limited to cardiac-associated IMDs and leads but may also be practiced with other electrical lead implantable for performing therapy and/or diagnosing in other body positions besides the heart, such as a neurological or muscle stimulating electrical lead.

Figure 4:
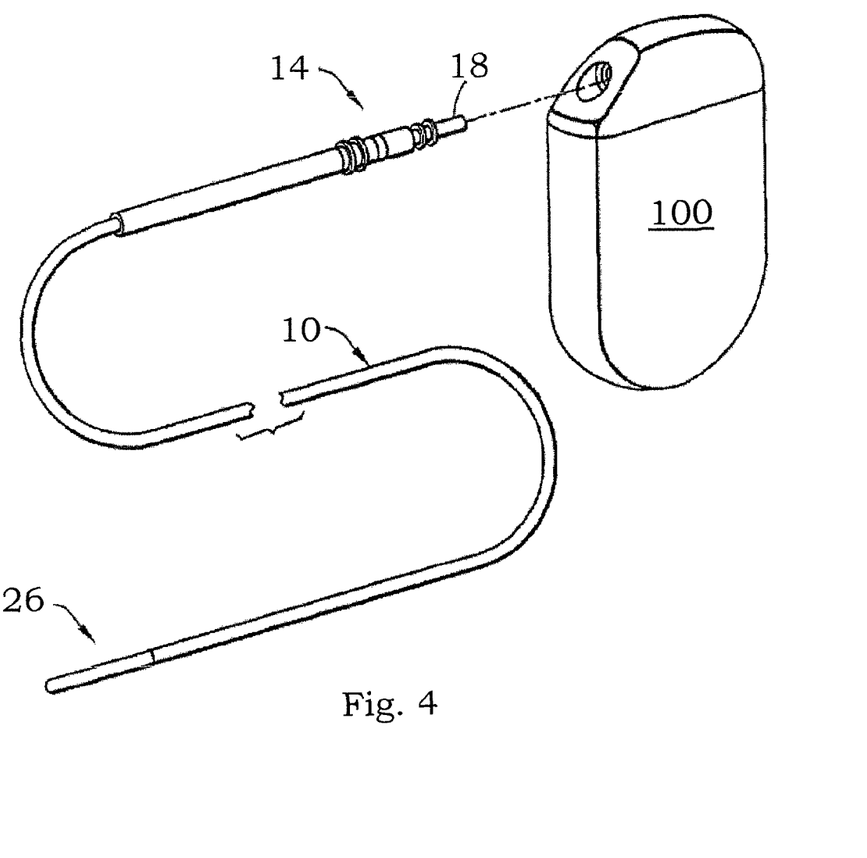
FIG. 4 illustrates an implantable electric lead connectable to an implantable medical device.

FIG. 4 schematically illustrates an IMD 100, exemplified as a pacemaker, connectable with an implantable electric lead 10 according to the present invention.

Figure 5:
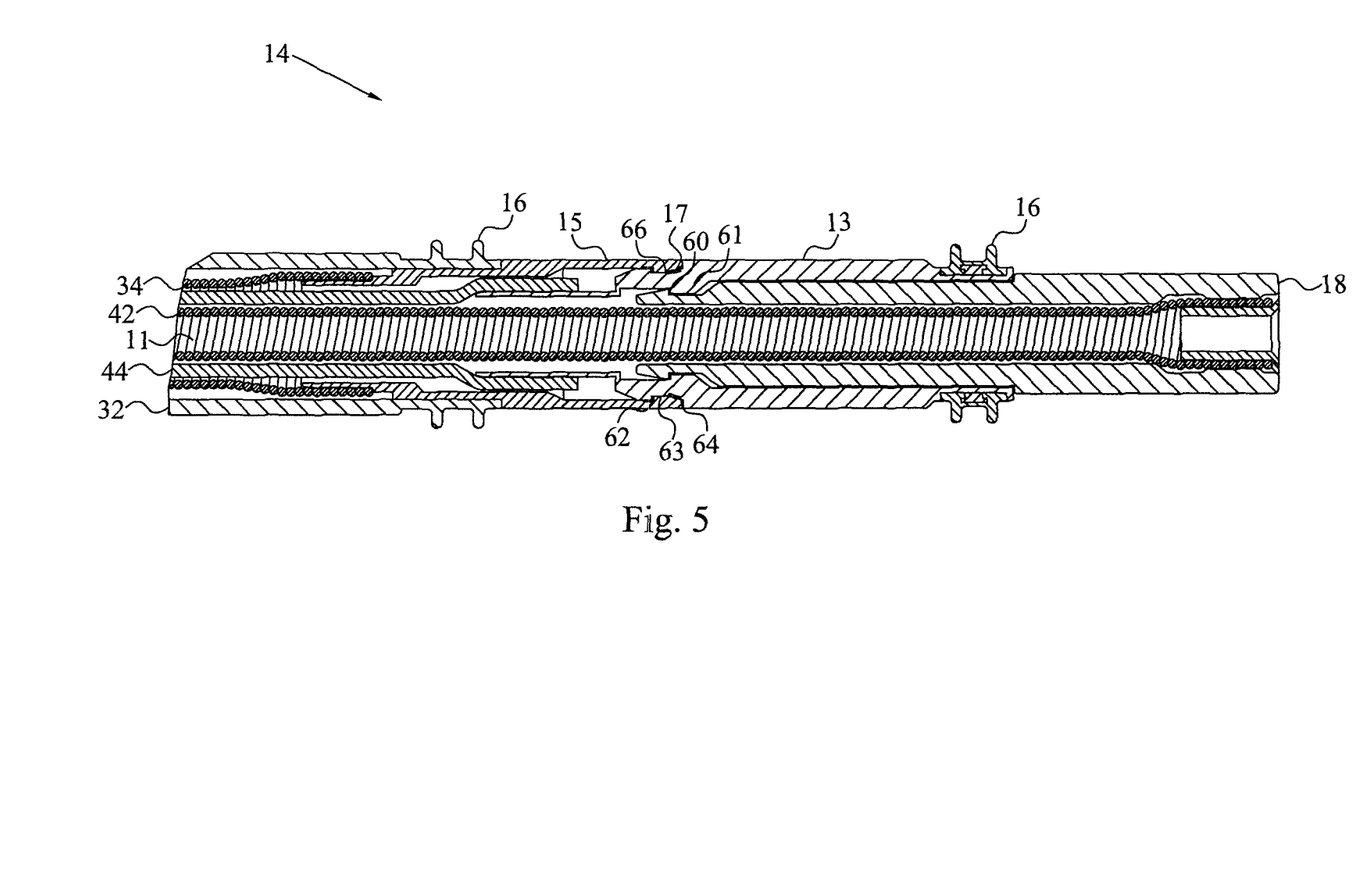
FIG. 5 is a cross-sectional view of a proximal portion of an implantable electric lead according to an embodiment.

FIG. 5 is cross-sectional view of the proximal lead portion 14 according to an embodiment. This proximal lead portion 14 comprises, in the present embodiment, three major interconnected components, a connector pin 18, a connector ring 15 and a connector coupling 13. The connector pin 18 is electrically connected to the inner connector 42 and is connectable to an IMD, which is schematically illustrated in FIG. 4. The connector pin 18 can generally be manufactured in the form of a cylinder of a conductive material, such as stainless steel, in particular 316L stainless steel, with the inner conductor 42 running in the bore of the connector pin 18 at least up to the end portion of the connector pin 18 designed to be connected to the IMD. Pin-conductor attachment can be effected by, for instance, welding to achieve not only an electrical connection between the connector pin 18 and the inner conductor 42 but also a mechanical attachment therebetween. Consequently, any rotation of the connector pin 18 is preferably transferred to a corresponding rotation of the inner conductor 42 as is further described herein.

The connector ring 15 is also made of a conductive material, such as 316L stainless steel, and is electrically connected to the outer conductor 34, typically at its end facing away from the IMD-connecting end of the lead. In similarity to the connector pin 18 and the inner conductor 42, the outer conductor 34 is preferably welded onto the connector ring 15 and may indeed be partly threaded on a portion of the connector ring 15 as illustrated in the figure to provide both an electrical connection and mechanical attachment between the connector ring 15 and the outer conductor 34. The two conductors 34, 42 run coaxially in the lumen 11 of the lead.

An outer insulative sheath 32 isolating the outer conductor 34 and the lead interior from the outside is attached to the connector ring 15, for instance by gluing. The outer insulative sheath 32 may be threaded over the outer conductor 34 and up to a portion of the lateral surface of the connector ring 15. A sealing ring 16 is advantageously attached in connection with the end of the insulative sheath 32 to prevent blood and other body fluids from entering the portion of the IMD, into which the proximal lead portion 14 is to be entered.

As is well known in the art, the connector ring 15 provides electrical connection between a distal electrode, typically a ring electrode, and an electrical terminal in the IMD through the outer conductor 34.

The connector coupling 13 is arranged in the proximal lead portion 14 for mechanically interconnecting the connector pin 18 and the connector ring 15. The connector coupling 13 is made of an insulating material in order to prevent any short circuits between the electrically conducting connector pin 18 and connector ring 15. The connector coupling 13 is preferably designed to be coaxially arranged around at least a portion of the connector pin 18, with the connector ring 15 correspondingly coaxially arranged around at least a portion of the connector coupling 13.

The mechanical connection between the connector pin 18 and the connector ring 15 effected by the connector coupling 13 should prevent or at least restrict any lateral or axial movement of these lead components relative each other. The connection should also allow the connector pin 18 with connected inner conductor 42 to be rotated relative the outer lead package, i.e. the outer insulative sheath 32, connector ring 15, outer conductor 34 and inner insulative sheath 42. This rotation of the inner lead package is used in connection with so-called active fixation leads as illustrated in FIGS. 1 and 2 in order to screw out and in the fixation helix at the distal lead portion to thereby anchor the lead at the target tissue. As a consequence, mechanical connections that prevent such rotations between the connector coupling 13 and the connector pin 18 are not preferred.

Figure 6:
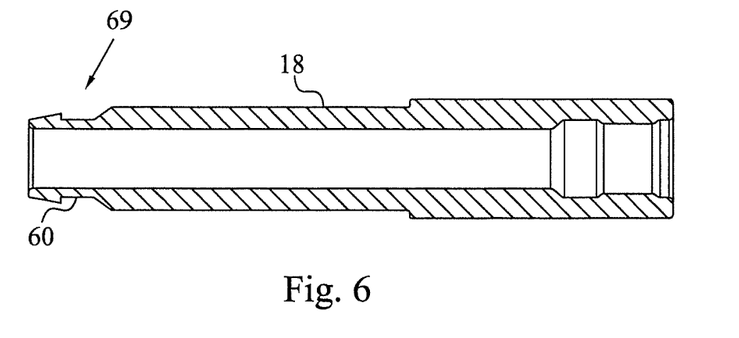
FIG. 6 is a cross-sectional view of a connector pin according to an embodiment.

A mechanical connection type that meets the above presented criteria, i.e. restricts axial movement but allows rotational movement, is a snap-fit lock. Such a snap-fit lock can be achieved by providing a circumferential or circumferentially distributed recess 60 in a connection portion 69 of the connector pin 18, which is more clearly illustrated in FIG. 6. The recess 60 preferably runs around the whole outer circumference in the lateral surface of the connector pin 18. Alternatively, although less preferred from assembling point of view as it requires alignment of the assembled lead components, the connector pin 18 can include one or more circumferentially distributed recesses 60.

Figure 7:
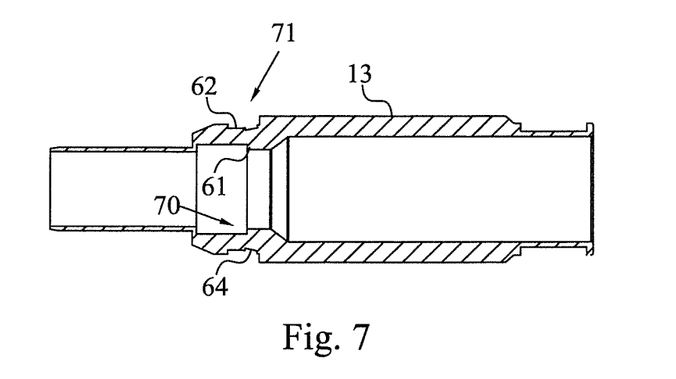
FIG. 7 is a cross-sectional view of a connector coupling according to an embodiment.

The connector coupling 13 then comprises a pin connecting portion 70, illustrated in FIG. 7, with a mating or matching latch 61 that is introduced in the recess 60 of the connector pin 18 when the connector coupling 13 is coaxially arranged around the connection portion 69 of the connector pin 18. Once the latch 61 enters the at least one recess 60, it effectively restrains any axial movement of the connector coupling 13 relative the connector pin 18. However, the resulting snap-fit lock allows the connector pin 18 to be rotated relative the connector coupling 13.

Alternatively, the mating latch is provided on the outer surface of the connector pin 18 with the recess present in the inner circumferential surface of the connector coupling 13.

A similar snap-fit lock solution can also be used to mechanically interconnect the connector ring 15 and the connector coupling 13. As is more clearly seen in FIG. 7, the connector coupling 13 consequently preferably has a circumferential or circumferentially distributed recess 62 provided in a ring connecting portion 71. In similarity to the recess 60 of the connector pin 18, this recess 62 is preferably provided all around the outer circumference in the lateral surface of the connector coupling 13, although one or more circumferentially distributed recesses 62 are indeed possible.

Figure 8:
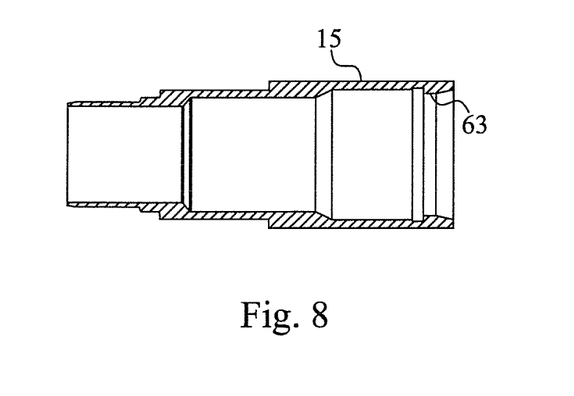
FIG. 8 is a cross-sectional view of a connector ring according to an embodiment.

The connector ring 15 comprises a matching latch 63, more clearly seen in FIG. 8, that is introduced in the recess 62 when the connector ring 15 is coaxially arranged around the ring connecting portion 71 of the connector coupling 13. Once introduced in the recess 62, the latch 63 effectively restrains any axial movement between the connector ring 15 and the connector coupling 13.

Alternatively, the mating latch is provided on the outer surface of the connector coupling 13 with the recess present in the inner circumferential surface of the connector ring 15.

In the above described snap-fit lock solutions, more than one locking latch can be used per snap-fit lock. Usage of multiple latches is in particular possible in connection with a matching recess provided around the whole circumferential or consisting of multiple circumferentially distributed recesses.

During implantation and in particular when rotating the connector pin 18, typically by means of a special tool, the operator may unintentionally also rotate the connector coupling 13 relative the outer insulative sheath 32 and the connector ring 15, due to the snap-fit locks not offering any significant rotation prevention. A similar problem can occur during the introduction and manipulation of the stylet assembly in FIG. 1 in the lumen of the lead. This can cause problems and even malfunctions to the lead as the inner insulative sheath 44 is mechanically connected to the connector coupling 13, typically by welding or gluing and preferably by being partly threaded upon the connector coupling 13 as illustrated in FIG. 5. Rotation of the connector coupling 13 is therefore transferred to a corresponding rotation of the inner insulative sheath 44. The inner insulative sheath 44 is mechanically attached in the distal lead portion and any rotation of the connector coupling 13 will cause the insulative sheath 44 to twist and may eventually break, causing the two conductors 34, 42 to short circuit.

The present invention solves these problems by introducing a rotation lock 17 in the interface between the connector coupling 13 and the connector ring 15. This rotational lock 17 is arranged for preventing or restraining rotation of the connector coupling 13 relative the connector ring 15. Any rotation of the connector pin 18 will then not be transferred to a rotation of the connector coupling 13 and the inner insulative sheath 44 as the rotational lock 17 effectively restricts the rotation of the connector coupling 13, which thereby becomes "locked" to the connector ring 15 and the outer lead package.

According to the invention, the rotational lock 17 is in the form a circumferential or circumferentially distributed element of an elastically deformable, flexible material that will function as a friction lock when being compressed between the connector ring 15 and the connector coupling 13.

The lock material is elastically deformable, which implies that if the connector ring 15 is disconnected from the connector coupling 13, the lock 17 assumes its original shape or at least substantially assumes the original shape. This feature is preferred as it causes the rotational lock 17 to tightly push against the connector ring 15 to restrict any rotation. The flexibility of the lock material is preferably adequate to allow it to be arranged in an outer surface of the connector coupling 13 with too stiff material not being capable of smoothly follow the curve of the outer connector coupling circumference.

In a first embodiment, the connector coupling 13 comprises a circumferential groove 64 in its outer surface 66. This groove 64 is present in the ring connecting portion 71 of the connector coupling 13, see FIG. 7, i.e. in the interface between the connector coupling 13 and the connector ring 15. The rotational lock 17 is arranged in the circumferential groove 64 and extends at least partly beyond the outer surface 66 in this portion of the connector coupling 13. When coaxially connecting the connector ring 15 onto the connector coupling 13, the rotational lock 17 becomes pressed between the coupling 13 and the ring 15 and effectively provides sufficient friction to prevent or at least significantly restrain any rotation between these two elements 13, 15.

Figure 10:
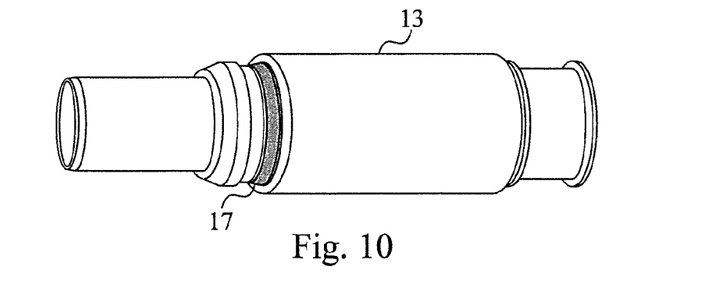
FIG. 10 is an illustration of a connector coupling with a sealing, rotational lock according to an embodiment.

FIG. 10 illustrates a side-view of the connector coupling 13 with a first embodiment of an rotational lock 17 provided in a circumferential groove 64 in the outer surface of the connector coupling 13. In a preferred embodiment, the rotational lock 17 is in the form of a sealing ring of the elastically deformable, flexible material that is coaxially positioned around the full circumference of the connector coupling 13 as illustrated in the figure. This embodiment not only achieves a rotational stop between the connector coupling 13 and the connector ring but also a sealing mechanism therebetween. Thus, when the connector ring is attached to the connector coupling 13 through the preferred snap-fit lock, the rotational lock 17 will be tightly pressed between the ring and the coupling 13 and prevent access to the interior of the lead. The dual-function of this embodiment relaxes the need for any dedicated sealing mechanism between the connector ring and the connector coupling 13 and prevents blood and other body fluids, etc. from entering the interior of the lead.

Figure 12:
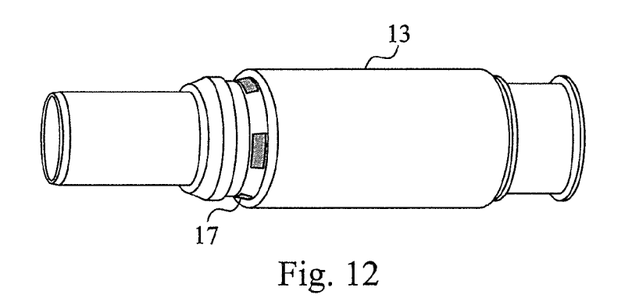
FIG. 12 is an illustration of a connector coupling with a rotational lock according to an embodiment.

Although a rotational lock 17 in the form of a ring as in FIG. 10 is preferred due to achieving an additional lead sealing, FIG. 12 illustrates an another embodiment of rotational lock 17. In this embodiment, the rotational lock 17 consists of one or more circumferentially distributed elements that are preferably present in dedicated indentations or grooves in the outer coupling surface. This embodiment achieves an efficient rotational lock in similarity to the embodiment in FIG. 10 but has the drawback of not providing any sealing mechanism of the lead interior.

Figure 9:
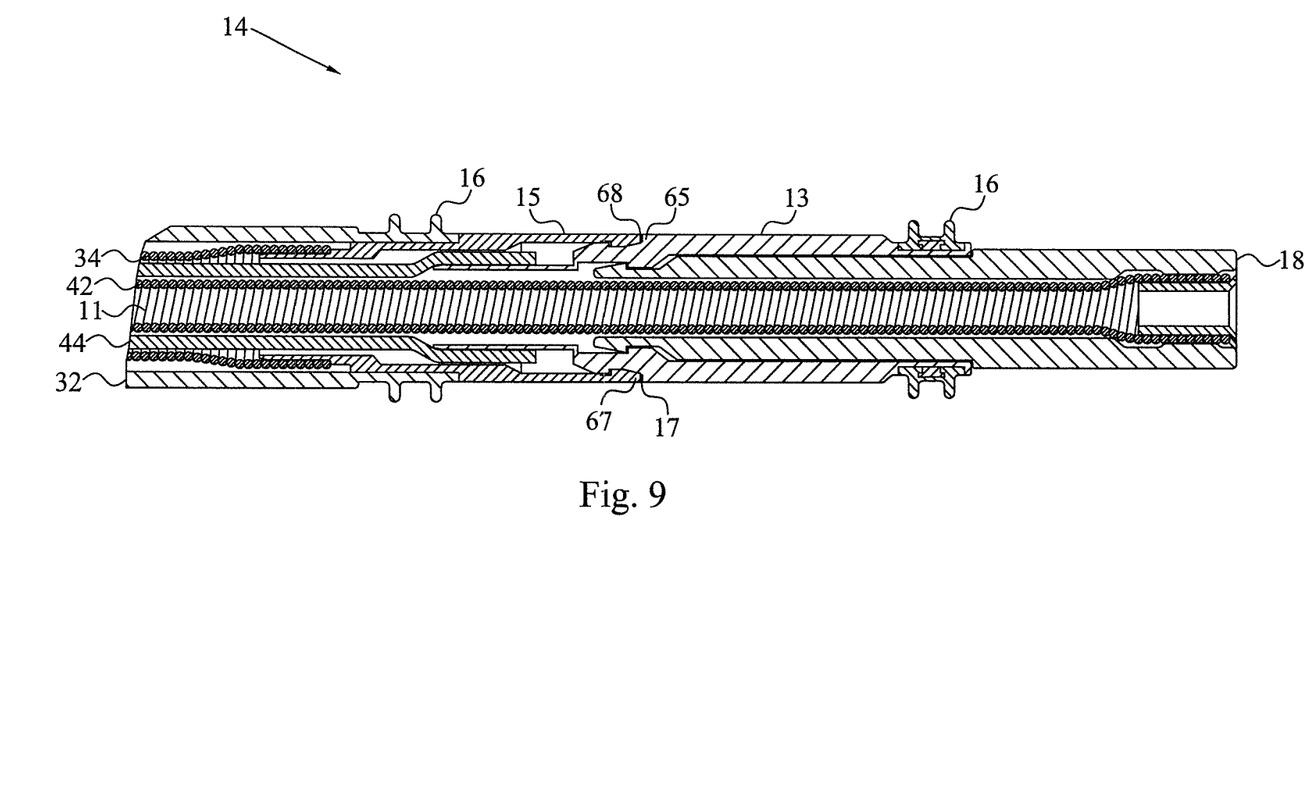
FIG. 9 is a cross-sectional view of a proximal portion of an implantable electric lead according to another embodiment.

FIG. 9 is a cross-sectional view of another embodiment of a proximal lead portion 14 of an implantable electric lead. In this embodiment, the rotational lock 17 is arranged in a surface 68 of a shoulder 65 of the connector coupling 13. This shoulder 65 is arranged in the connector coupling 13 so that an end 67 of the connector ring 15 bears on the lock-comprising surface 68 of the shoulder 65. As is seen in the figure, the surface 68 faces the end 67 of the connector ring 15 so that the rotational lock 17 is provided in the interface between the ring 15 and the connector coupling 13.

Figure 11:
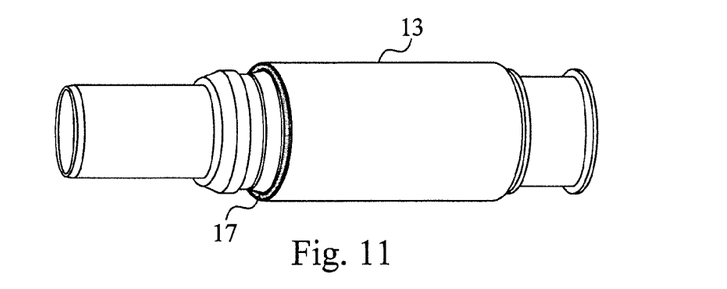
FIG. 11 is an illustration of a connector coupling with a sealing, rotational lock according to another embodiment.

FIG. 11 illustrates a side-view of a connector coupling with the rotational lock 17 provided in the ring-facing surface of its shoulder. In the figure, the rotational lock 17 has been illustrated as the preferred sealing ring that not only provides a friction and rotational lock mechanism but also a sealing mechanism to seal the interior of the lead from the outside. In similarity to the embodiment disclosed in FIG. 12, in an alternative approach the rotational lock 17 could, though less preferred, be in the form of one or more circumferentially distributed elements in the shoulder surface.

The shoulder surface preferably has a circumferential groove or one or more indentions in which the rotational lock 17 is provided to extend at least partly beyond the shoulder surface.

Figure 13:
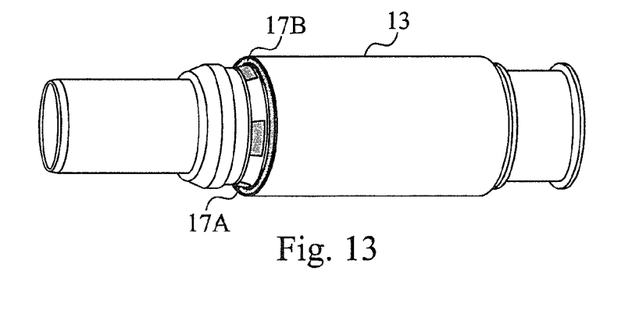
FIG. 13 is an illustration of a connector coupling with multiple rotational locks and sealing according to a further embodiment.

A shoulder-arranged rotational lock 17B may be combined with a rotational lock 17A provided in the lateral connector surface, which is illustrated in FIG. 13. In such a case, at least one of the rotational locks 17B is preferably in the form of a ring in order to also achieve the desired sealing mechanism, though both rotational locks 17A, 17B can indeed be in the form of rings. Usage of multiple rotational locks 17A, 17B can be advantageous in order to provide a more secure rotational stop as compared to having a single rotational lock. However, in most practical situations one rotational lock would be sufficient.

In the above presented embodiments the rotational lock has been arranged in the connector coupling in the interface between the coupling and the connector ring. This is the preferred position since if the rotational lock instead would be present in the inner circumferential surface of the connector ring, it could be pushed or peeled off when the connector ring is coaxially attached around the connector coupling.

The elastically deformable, flexible material of the rotational lock is preferably molded onto the connector coupling. Other attachment techniques, such as gluing or passive attachment similar to an O-ring, are also possible and within the scope of the invention.

The elastically deformable, flexible material should also be biocompatible, i.e. elicit little or no immune response and generally be non-toxic, when implanted in the animal body. Preferred materials are therefore selected among materials having been approved for medical devices and implantation.

A preferred elastically deformable, flexible material that has proven to be effective as sealing, rotational lock and is biocompatible is silicone, preferably silicone rubber. The silicone rubber can, for instance, be MED-4870 silicone rubber from NuSil Technology or SILASTIC® biomedical grade silicone rubber from Dow Corning.

The rotational lock of the embodiments achieves the desired rotation restricting effect without any accompanying drawbacks in the form of increased complexity of the proximal lead portion, its including lead components or the assemble thereof. Thus, providing the rotational lock in the interface between the connector ring and coupling does not bring about any complex design changes to the components and does not cause additional, complex operation steps to the assemble of the proximal lead portion. In clear contrast, the rotational lock can even contribute to a reduction in lead components as no extra sealing components between the connector coupling and ring are need for some of the embodiments.

A further advantage of the rotational lock of the invention is that is can be manufactured at low cost using currently available materials.

Figure 14:
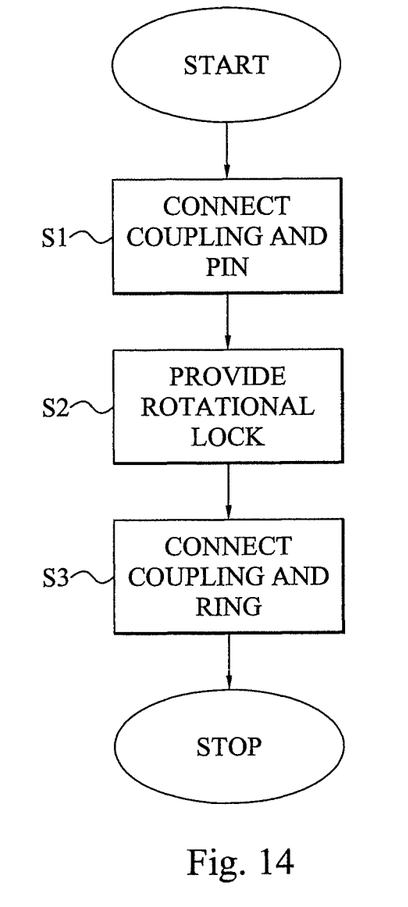
FIG. 14 is a flow diagram illustrating a method of assembling an implantable electric lead according to an embodiment.

FIG. 14 is a schematic flow diagram of a method of assembling an implantable electric lead according to an embodiment. The implantable electric lead comprises a lead body with a lumen, a distal lead portion comprising at least one electrode and at least one conductor that is electrically connected to a respective electrode and designed to run in the lumen. The assembly process generally starts in step S1 which involves mechanically and coaxially connecting a connector coupling and a connector pin to restrain any axial movement between the connector coupling and pin but allow a rotation between these two components. The connection can be in the form of introducing a connecting portion of the connector pin in the bore of the connector pin up until a latch of the connector pin enters a matching recess in the connector pin to form a snap-fit lock.

Step S2 provides a rotational lock in the form of a circumferential or circumferentially distributed element of an elastically deformable, flexible material in the connector coupling. This provision can be in the form of molding the rotational lock in a dedicated groove in the outer connector coupling surface and/or in a shoulder surface of the connector coupling. Other attachment techniques as mentioned above can be used.

Step S2 can be performed after step S1 as illustrated in the figure or indeed prior to step S1.

A next step S3 mechanically and coaxially connects the connector coupling and the connector ring to restrain any axial movement between the two elements. This connection can be effected by the previously described snap-fit solution. Connecting these two elements will compress the rotation lock between the connector ring and coupling in the interface therebetween to restrain any rotation of the connector coupling relative the connector ring.

Step S3 is conducted after step S2 but may be performed prior step S1, basically achieving an alternative assembly order according to step S2, S3 and finally step S1 or step S2, S1 and then step S3.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

Although modifications and changes may be suggested by those skilled in the art, it is the intention of the inventors to embody within the patent warranted heron all changes and modifications as reasonably and properly come within the scope of their contribution to the art.

We claim as our invention:

1. An implantable electric lead comprising:
   a lead body comprising a lumen;
   a distal lead portion comprising an electrode;
   a conductor electrically connected to said electrode and running in said lumen;
   a proximal lead portion comprising:
      a connector pin connectable to an implantable medical device;
      a connector ring electrically connected to said conductor;
      a connector coupling mechanically interconnecting said connector pin and said connector ring, said connector pin, said connector ring and said connector coupling being co-axially arranged relative each other in said proximal lead portion; and
      a rotational lock formed by a circumferential or circumferentially distributed element of an elastically deformable, flexible material in said connector coupling in an interface between said connector coupling and said connector ring and arranged for restraining rotation of said connector coupling relative said connector ring.

2. The implantable electric lead according to claim 1, wherein said rotational lock is formed by a sealing ring of said elastically deformable, flexible material coaxially positioned around said connector coupling.

3. The implantable electric lead according to claim 1, wherein said connector coupling comprises a circumferential groove in an outer surface thereof, said rotational lock being arranged in said circumferential groove.

4. The implantable electric lead according to claim 1, wherein said connector coupling comprises a shoulder on which an end of said connector ring bears, said rotational lock being arranged in a surface of said shoulder facing said end of said connector ring.

5. The implantable electric lead according to claim 1, wherein said rotational lock is molded onto said connector coupling.

6. The implantable electric lead according to claim 1, wherein said elastically deformable, flexible material is silicone.

7. The implantable electric lead according to claim 6, wherein said silicone is selected from the group consisting of NuSil MED-4870 silicone elastomer and SILASTIC® 7-6860 biomedical grade liquid silicone rubber.

8. The implantable electric lead according to claim 1, wherein said connector pin is formed by a cylindrical element having a connection portion with a circumferential or circumferentially distributed recess; and wherein said connector coupling comprises:
   a pin connecting portion coaxially arranged around said connection portion with a latch introduced in said recess of said connector pin to restrain any axial movement of said connector coupling relative said connector pin; and
   a ring connecting portion with a circumferential or circumferentially distributed recess; and said connector ring comprising a latch introduced in said recess of said connector coupling to restrain any axial movement of said connector ring relative said connector coupling.

9. The implantable electric lead according to claim 1, wherein said electrode is a ring electrode and said conductor is an outer coiled conductor electrically interconnecting said ring electrode and said connector ring, said implantable electric lead further comprising:
   a fixation helix mechanically connected, at said distal lead portion, to an inner coiled conductor running coaxially in said lumen relative said outer coiled conductor and being mechanically and electrically connected to said connector pin to transfer a rotation of said connector pin to a rotation of said fixation helix; and an insulative sheath attached to said connector coupling and arranged around said inner coiled conductor electrically isolate said inner coiled conductor from said outer coiled conductor.

10. A method of assembling an implantable electric lead comprising a lead body having a lumen, a distal lead portion comprising an electrode, and a conductor electrically connected to said electrode and running in said lumen, said method comprising:

mechanically and coaxially connecting a connector coupling and a connector pin designed to be connectable to an implantable medical device to restrain any axial movement between said connector coupling and said connector pin but allow a rotation of said connector pin relative said connector coupling;

providing a rotational lock in the form of a circumferential or circumferentially distributed element of an elastically deformable, flexible material in said connector coupling; and mechanically and coaxially connecting said connector coupling and a connector ring electrically connected to said conductor to restrain any axial movement between said connector coupling and said connector ring, and arranging said rotational lock in an interface between said connector coupling and said connector ring to restrain rotation of said connector coupling relative said connector ring.

* * * * *